United States Patent
Fukuoka et al.

(10) Patent No.: US 9,480,813 B2
(45) Date of Patent: Nov. 1, 2016

(54) CORONARY ARTERY CATHETER AND ENGAGING METHOD THEREFOR

(71) Applicant: Terumo Kabushiki Kaisha, Tokyo (JP)

(72) Inventors: Tetsuya Fukuoka, Fujinomiya (JP); Yuya Otake, Fujinomiya (JP); Mariko Ueda, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 524 days.

(21) Appl. No.: 13/926,546

(22) Filed: Jun. 25, 2013

(65) Prior Publication Data

US 2014/0025041 A1 Jan. 23, 2014

(30) Foreign Application Priority Data

Jul. 20, 2012 (JP) ................... 2012-161035

(51) Int. Cl.
*A61M 25/00* (2006.01)
*A61M 25/06* (2006.01)

(52) U.S. Cl.
CPC .......... *A61M 25/00* (2013.01); *A61M 25/005* (2013.01); *A61M 25/0041* (2013.01); *A61M 2025/0681* (2013.01); *A61M 2210/125* (2013.01)

(58) Field of Classification Search
CPC .......... A61M 25/00; A61M 25/0041; A61M 25/005; A61M 2025/0681
USPC ....................................... 604/523
See application file for complete search history.

(56) References Cited

U.S. PATENT DOCUMENTS

| 5,322,509 | A | 6/1994 | Rickerd |
| 5,603,704 | A | 2/1997 | Brin et al. |
| 5,885,247 | A * | 3/1999 | Slagboom ......... A61M 25/0041 604/200 |
| 5,916,209 | A | 6/1999 | Mick |
| 5,971,974 | A | 10/1999 | Keisz |
| 6,475,195 | B1 | 11/2002 | Voda |
| 7,747,334 | B2 * | 6/2010 | Bly ................. A61N 1/056 607/122 |
| 2009/0082756 | A1 * | 3/2009 | Vidyarthi .......... A61M 25/0041 604/527 |
| 2011/0071503 | A1 * | 3/2011 | Takagi ............ A61M 25/0041 604/532 |

FOREIGN PATENT DOCUMENTS

| EP | 0 728 494 A1 | 8/1996 |
| WO | 97/09087 A1 | 3/1997 |

OTHER PUBLICATIONS

European Search Report dated Oct. 21, 2013, issued in corresponding European Patent Application No. 13175758.5.

* cited by examiner

*Primary Examiner* — Laura Bouchelle
(74) *Attorney, Agent, or Firm* — Buchanan Ingersoll & Rooney PC

(57) ABSTRACT

A coronary artery catheter adapted for introducing its distal end into a coronary ostium through an artery includes a catheter body with a lumen formed therein. The catheter body in a natural state includes: a proximal straight section extending distally from a proximal end of the catheter body; a first curved section extending distally from the proximal straight section while being curved; an intermediate straight section extending distally from the first curved section; a second curved section extending distally from the intermediate straight section while being curved; and a distalmost section extending from the second curved section to a distal end of the catheter body. The first curved section and the second curved section, when projected onto a plane on which the first curved section and the intermediate straight section are present, curve in the same direction.

4 Claims, 6 Drawing Sheets

CORONARY ARTERY CATHETER AND ENGAGING METHOD THEREFOR

CROSS-REFERENCE TO RELATED APPLICATION

This application claims priority to Japanese Patent Application No. 2012-161035 filed on Jul. 20, 2012, the entire content of which is incorporated herein by reference.

TECHNICAL FIELD

The present invention relates to a coronary artery catheter for use in therapy or imaging of the heart or the surroundings thereof and to an engaging method for the coronary artery catheter.

BACKGROUND

Conventionally, a coronary angiography catheter has been used to supply a radiopaque material (contrast agent) into a coronary artery for imaging the coronary artery.

In addition, treatments of peripheral regions of a patient by use of a catheter or catheters have been widely practiced. One example of such treatments is the percutaneous transluminal coronary angioplasty (PTCA) as a treatment of ischemic cardiopathy based on the use of a therapeutic catheter equipped with an inflatable balloon. In such a treatment, in order to insert the therapeutic catheter into a target blood vessel safely and efficiently and to permit the therapeutic catheter to display a sufficient function in a target site, a guiding catheter is needed. In this case, the guiding catheter provides a backup force so as to relax counteractions arising from the insertion of the therapeutic catheter and to keep the therapeutic catheter in a desired position.

An example of such system is described in U.S. Pat. No. 6,475,195 (hereinafter referred to as Patent Document 1) and U.S. Pat. No. 5,603,704 (hereinafter referred to as Patent Document 2). In this example, a guiding catheter having its distal end engaged in the left coronary ostium makes linear contact with the ascending aorta inner wall opposite to the left coronary ostium, whereby a backup force is generated.

Such a coronary angiography catheter or guiding catheter is normally introduced from a femoral artery by the Seldinger technique, or sheath technique. After the coronary artery is selectively captured by the angiography or guiding catheter, a radiopaque material or a therapeutic catheter such as a PTCA balloon catheter is introduced through the lumen provided inside the angiography or guiding catheter.

SUMMARY

In the angiography or treatment based on the use of a coronary artery catheter as above-mentioned, the catheter is normally introduced from a femoral region. After the operation, therefore, bed rest as well as compression of the punctured part for a long time for hemostasis is needed. Thus, this approach imposes a heavy burden on the patient.

In view of this, a method of introducing a coronary artery catheter from an artery of an arm, particularly a brachial artery or a radial artery, has been proposed in recent years. When the coronary artery catheter is introduced from an artery of an arm, the compression time and recovery time after the operation can be shortened, so that the burden on the patient can be lessened.

However, the guiding catheter described in the above-mentioned Patent Document 1 has a structure in which a bent section for separating the guiding catheter from the inner wall of the ascending aorta is formed on the proximal side of the guiding catheter part that is making linear contact with the ascending aorta inner wall and thereby giving a backup force. When this guiding catheter is introduced from an artery of an arm, therefore, the catheter passes through the brachiocephalic trunk into the aorta and then toward the coronary artery, thereby being bent in the direction opposite to the direction of the bent section. Although this bending causes generation of a backup force, the backup force owing to the bending is not displayed sufficiently, since the bent section curved in the direction opposite to the bending is present on the distal side relative to the part of the bending.

On the other hand, the guiding catheter described in the above-mentioned Patent Document 2 has a structure in which the whole body of the catheter is curved in one direction. When this guiding catheter is introduced from an artery of an arm, therefore, the catheter passes through the brachiocephalic trunk into the aorta and then toward the coronary artery, resulting in that the curved guiding catheter is bent in the direction opposite to the direction of curvature. This may cause an excessive backup force to be generated.

The present invention has been made in order to solve the above-mentioned problems. Accordingly, it is desirable that the present invention provides a coronary artery catheter which can be favorably engaged in an artery through the generation of an appropriate backup force.

According to an embodiment of the present invention, there is provided a coronary artery catheter adapted for introducing its distal end into a coronary ostium through an artery, the coronary artery catheter having a catheter body with a lumen formed therein, the catheter body in a natural state including: a proximal straight section being originally straight; a first curved section extending distally from the proximal straight section while being curved; an intermediate straight section being originally straight and extending distally from the first curved section; a second curved section extending distally from the intermediate straight section while being curved; and a distalmost section extending from the second curved section to a distal end of the catheter body, in which directions of curvature of the first curved section and the second curved section projected onto a plane on which the first curved section and the intermediate straight section are present coincide with each other.

The coronary artery catheter configured as above may be used in a condition in which at least part of the second curved section is put in contact with an inner wall of an ascending aorta opposite to the coronary ostium so as to function as a backup support, while the first curved section is bent in a direction opposite to a direction of curvature in its original shape, and the resilience or repulsive force generated by this bending is made to act as an appropriate backup force through the intermediate straight section being originally straight. When the coronary artery catheter is used in this condition, the catheter is favorably engaged with the arteries.

The coronary artery catheter may be so configured that when the coronary artery catheter is introduced through an artery of an arm and the distalmost section is engaged with the coronary ostium, the intermediate straight section is disposed both inside an aorta and inside a brachiocephalic trunk, and the first curved section is disposed inside the brachiocephalic trunk. This configuration ensures that an appropriate backup force can be transmitted distally through the intermediate straight section which is disposed both inside the aorta and inside the brachiocephalic trunk, in a condition in which the first curved section is bent in the opposite direction, not inside the ascending aorta but inside the brachiocephalic trunk, thereby producing a backup force.

The coronary artery catheter may be so configured that when the coronary artery catheter is introduced through an artery of an arm and the distalmost section is engaged with the coronary ostium, the distalmost section extends from a position, on an aortic valve side relative to the coronary ostium, in the ascending aorta toward the coronary ostium, and an axis of the distalmost section is inclined relative to an axis of the coronary ostium; the distalmost section and part of the second curved section are curved in a same first direction; part of the second curved section makes linear contact with an inner wall of the ascending aorta opposite to the coronary ostium; the intermediate straight section is disposed inside the ascending aorta and inside the brachiocephalic trunk in a state where its distal portion is curved in the first direction whereas its proximal portion is curved in a second direction opposite to the first direction; the first curved section is disposed inside the brachiocephalic trunk in a state of being curved in the second direction; and the proximal straight section is disposed inside the brachiocephalic trunk or inside a right subclavian artery in a state of being curved in the second direction, and at least part thereof makes linear contact with an inner wall of the brachiocephalic trunk or an inner wall of the right subclavian artery. This configuration ensures that the catheter body is favorably supported in the arteries by the functions of the distalmost section which is engaged with the coronary ostium, the second curved section which is engaged with the inner wall of the ascending aorta, and the proximal straight section which is engaged with the inner wall of the brachiocephalic trunk or the right subclavian artery. In addition, since the distalmost section extends from the position, on the aortic valve side relative to the coronary ostium, in the ascending aorta toward the coronary ostium and the axis of the distalmost section is inclined relative to the axis of the coronary ostium, a force for clamping something between the distalmost section and the second curved section is generated in the vicinity of the coronary ostium. Due to this force, the distalmost section will hardly be disengaged from the coronary ostium. In addition, since the intermediate straight section has an inflection point, generation of an excessive backup force is restrained. Moreover, the axis of the distalmost section is inclined relative to the axis of the coronary ostium. Consequently, excessive insertion of the catheter body into the coronary artery is restrained.

The coronary artery catheter may be so configured that when the coronary artery catheter is introduced through an artery of an arm and the distalmost section is engaged with the coronary ostium, the distalmost section makes linear contact with an inner wall of the coronary artery; at least part of the second curved section makes linear contact with the inner wall of the ascending aorta opposite to the coronary ostium while being curved in the first direction; the intermediate straight section is disposed inside the ascending aorta and inside the brachiocephalic trunk in a state of being curved in the second direction opposite to the first direction; the first curved section is disposed inside the brachiocephalic trunk in a state of being curved in the second direction; and the proximal straight section is disposed inside the brachiocephalic trunk or inside the right subclavian artery in a state of being curved in the second direction, and at least part thereof makes linear contact with the inner wall of the brachiocephalic trunk or the inner wall of the right subclavian artery. This configuration ensures that the catheter body is favorably supported in the arteries by the functions of the distalmost section which is inserted in and engaged with the coronary artery, the second curved section which is engaged with the inner wall of the ascending aorta, and the proximal straight section which is engaged with the inner wall of the brachiocephalic trunk or the right subclavian artery. Besides, since the intermediate straight section being originally straight is bent, generation of an excessive backup force is restrained. Consequently, excessive insertion of the catheter body into the coronary artery is restrained.

The coronary artery catheter may be so configured that when the coronary artery catheter is introduced through a femoral artery and the distalmost section is engaged with the coronary ostium, the distalmost section makes linear contact with the inner wall of the coronary artery; and a proximal-side portion of the second curved section, the intermediate straight section, the first curved section, and at least a distal-side portion of the proximal straight section make continuous and linear contact with an inner wall, opposite to the coronary ostium, of the aorta including the ascending aorta, an aortic arch and a descending aorta while being curved in the first direction. This configuration ensures that the catheter body is favorably supported in the arteries by the functions of the distalmost section which is engaged with the coronary ostium, as well as the second curved section, the intermediate straight section, the first curved section and the proximal straight section which are engaged with the inner wall of the aorta. Incidentally, the second curved section, the intermediate straight section, the first curved section and the proximal straight section are being curved in the same direction as their direction of curvature in a natural state. This restrains generation of an excessive backup force. Consequently, excessive insertion of the catheter body into the coronary artery is restrained.

According to another embodiment of the present invention, there is provided a method of engaging a coronary artery catheter, adapted for introducing its distal end into a coronary ostium through an artery of an arm, with the coronary ostium. The coronary artery catheter has a catheter body with a lumen formed therein, the catheter body in a natural state including: a proximal straight section being originally straight; a first curved section extending distally from the proximal straight section while being curved; an intermediate straight section being originally straight and extending distally from the first curved section; a second curved section extending distally from the intermediate straight section while being curved; and a distalmost section extending from the second curved section to a distal end of the catheter body, with directions of curvature of the first curved section and the second curved section projected onto a plane on which the first curved section and the intermediate straight section are present coinciding with each other. The method includes: engaging the distalmost section with the coronary ostium; bringing the second curved section into linear contact with an inner wall of an ascending aorta opposite to the coronary ostium; disposing the intermediate straight section both inside the ascending aorta and inside a brachiocephalic trunk; and disposing the first curved section inside the brachiocephalic trunk. This method ensures that an appropriate backup force can be transmitted distally through the intermediate straight section which is disposed both inside the ascending aorta and inside the brachiocephalic trunk, in a condition in which the first curved section is bent in the opposite direction, not inside the ascending aorta but inside the brachiocephalic trunk, thereby producing a backup force.

According to another aspect of the disclosure, a coronary artery catheter adapted for introducing its distal end into a coronary ostium through an artery has a catheter body with a lumen formed therein. The catheter body in a natural state includes a main body proximal portion and a main body distal portion on the distal side of the main body proximal portion. The main body distal portion includes a proximal straight section being originally straight, a first curved section extending distally from the proximal straight section while being curved, an intermediate straight section being originally straight and extending distally from the first curved section, a second curved section extending distally from the intermediate straight section while being curved, and a distalmost section extending from the second curved section to a distal end of the catheter body. The proximal straight section and the main body proximal portion form a continuous substantially straight section. The first curved section and the second curved section, when projected onto a plane on which the first curved section and the intermediate straight section are present, curve in the same direction.

DETAILED DESCRIPTION

Figure 1:
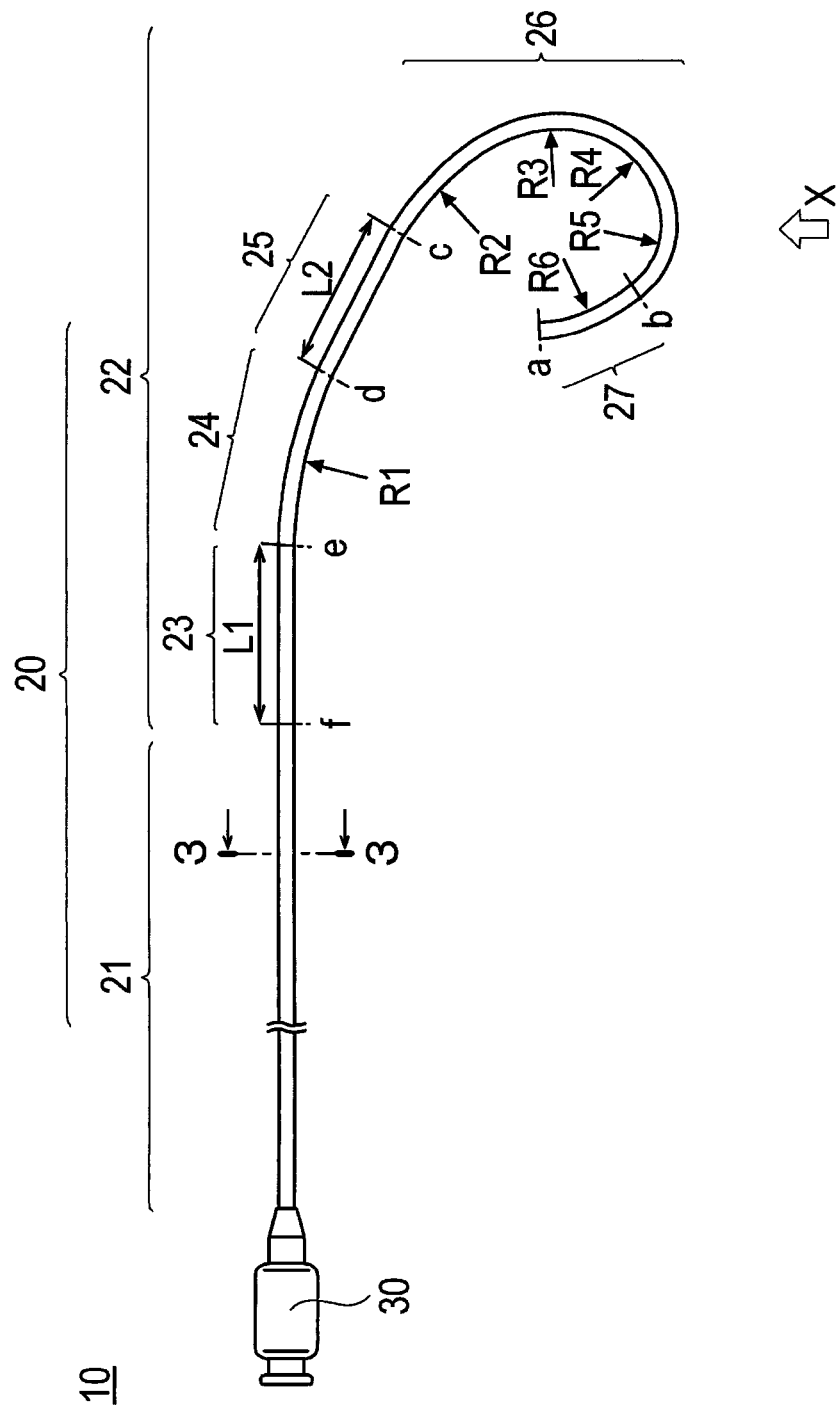
FIG. 1 is a plan view of a coronary artery catheter according to an embodiment of the present invention.

Now, an embodiment of the present invention will be described below referring to the drawings. Incidentally, dimensional ratios in the drawings may be exaggerated, for convenience of description, so as to be different from actual ratios. With respect to a coronary artery catheter herein, the side of insertion into a lumen will be referred to as "distal" or "distal side," and the side of operation by hand will be referred to as "proximal" or "proximal side."

Figure 5:
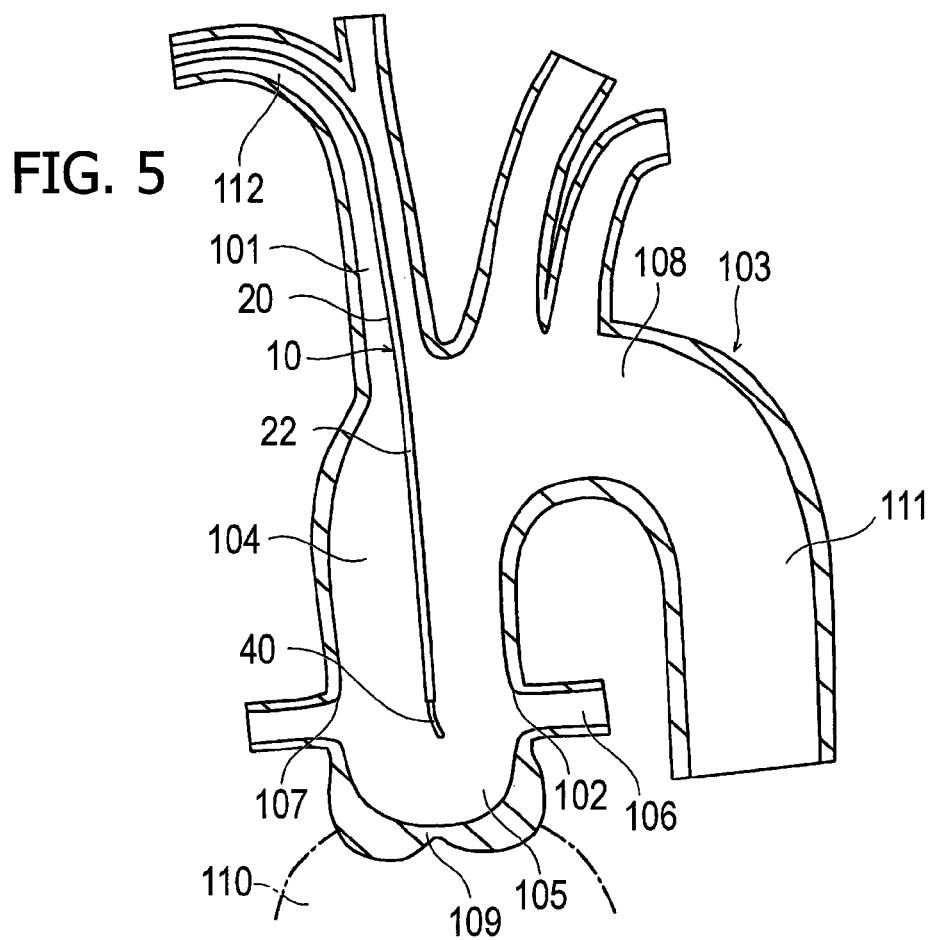
FIG. 5 is a schematic illustration of a state in which the coronary artery catheter according to the present embodiment is introduced from an artery of an arm and its distal end is brought into the vicinity of a left coronary ostium.

A coronary artery catheter 10 according to an embodiment of the present invention (hereafter referred also to simply as "catheter 10") is adapted for introducing its distal end from an artery of a left or right arm (particularly, an artery of a right arm) into a left or right coronary ostium (particularly, a left coronary ostium 102—see FIG. 5). Incidentally, the coronary artery catheter 10 according to the present embodiment may have its distal end introduced from a femoral artery into the left or right coronary ostium.

As shown in FIG. 1, the catheter 10 has a flexible catheter body 20 of a hollow structure, and a hub 30 connected to a proximal portion of the catheter body 20. The hub 30 functions as an injection port at the time of injecting a radiopaque material (i.e., contrast agent for imaging) or an insertion port through which to insert a therapeutic instrument.

In order that the catheter 10 can be introduced from a human brachial artery, preferably a human radial artery 100 (see FIG. 4), an outside diameter of the catheter body 20 is set to be not more than about 2.7 mm (preferably, not more than about 2.1 mm) over the whole length thereof. The catheter 10 introduced from the arm is passed through a right subclavian artery 112 and a brachiocephalic trunk 101 (see FIG. 5), to reach an ascending aorta 104.

The catheter body 20 includes a main body proximal portion 21 which is straight in a natural state, and a main body distal portion 22 which is provided on the distal side of the main body proximal portion 21 and is formed in a predetermined shape in a natural state. The expression "a natural state" means a state in which no external force is exerted, here and hereafter.

The main body proximal portion 21 is substantially straight (roughly straight line-shaped) in a natural state. The length of the main body proximal portion 21 is not particularly limited, and may range from about 400 to 1,200 mm.

The main body distal portion 22 includes: a proximal straight section 23 extending from the main body proximal portion 21; a first curved section 24 extending distally from the proximal straight section 23 while being curved; an intermediate straight section 25 being originally straight and extending distally from the first curved section 24; a second curved section 26 extending distally from the intermediate straight section 25 while being curved; and a distalmost section 27 extending from the second curved section 26 to the distal end of the main body distal portion 22 (of the catheter body 20). The proximal straight section 23, the first curved section 24 and the intermediate straight section 25 are present on substantially a same plane A (see FIG. 2).

The proximal straight section 23 is located over a range from a position (e) to a position (f) shown in FIG. 1, and is substantially straight (roughly straight line-shaped) in a natural state. The proximal straight section 23 is formed to be continuous with the main body proximal portion 21. A length L1 of the proximal straight section 23 can be selectively determined, as required.

The first curved section 24 is located over a range from a position (d) to the position (e) shown in FIG. 1, and is formed to be curved in one direction in a natural state. The first curved section 24 is preferably so set that, in a natural state, its curvature radius R1 is about 60 to 150 mm, for example, and an extension angle of the curvature radius R1 (an angular range of extension about a center of curvature) is about 10 to 30°, for example. In the configuration example shown in FIG. 1, the curvature radius R1 of the first curved section 24 is set to be about 84 mm, and the extension angle is set to be about 21°. The first curved section 24 is preferably disposed in the brachiocephalic trunk 101 when the coronary artery catheter 10 is introduced through the artery of the arm and its distalmost section 27 is engaged with the left coronary ostium 102, which is an opening of a left coronary artery 106 (see FIGS. 6 and 7).

The intermediate straight section 25 is located over a range from a position (c) to the position (d) shown in FIG. 1, and is substantially straight (roughly straight line-shaped) in a natural state. A length L2 of the intermediate straight section 25 is preferably about 15 to 40 mm, for example. In the configuration example shown in FIG. 1, the length L2 of the intermediate straight section 25 is about 27 mm. The intermediate straight section 25 is preferably disposed both inside an aorta 103 and inside the brachiocephalic trunk 101 when the coronary artery catheter 10 is introduced through the artery of the arm and its distalmost section 27 is engaged with the left coronary ostium 102 (see FIGS. 6 and 7).

The second curved section 26 is located over a range from a position (b) to the position (c) shown in FIG. 1, and is so formed as to be curved in one direction in a natural state. The second curved section 26 is so formed that its curvature radius gradually decreases from the proximal end toward the distal end. The second curved section 26 is so formed that curvature radii R2 to R5 are arranged in this order from the proximal side in a natural state. Preferably, for example, the shape including these curvature radii R2 to R5 are so set that the curvature radius R2 is about 20 to 50 mm, the extension angle of the curvature radius R2 is about 20 to 70°, the curvature radius R3 is about 10 to 40 mm, the extension angle of the curvature radius R3 is about 20 to 90°, the curvature radius R4 is about 10 to 40 mm, the extension angle of the curvature radius R4 is about 20 to 90°, the curvature radius R5 is about 10 to 40 mm, and the extension angle of the curvature radius R5 is about 20 to 90°. In the configuration example shown in FIG. 1, the second curved section 26 is so shaped that the curvature radius R2 is about 39 mm, the extension angle of the curvature radius R2 is about 35°, the curvature radius R3 is about 21 mm, the extension angle of the curvature radius R3 is about 66°, the curvature radius R4 is about 17 mm, the extension angle of the curvature radius R4 is about 53°, the curvature radius R5 is about 14 mm, and the extension angle of the curvature radius R5 is about 57°. The curvature radii of the second curved section 26 are preferably set to be greater than an inside radius of the ascending aorta 104 (see FIG. 5).

The distalmost section 27 is located over a range from a position (a) to the position (b) shown in FIG. 1, and is so formed as to be curved in one direction in a natural state. The distalmost section 27 is preferably so set that its curvature radius R6 is about 20 to 150 mm, for example, and the extension angle of the curvature radius R6 is about 5 to 50° in a natural state, for example. The curvature radius R6 is greater than the curvature radius R5 of the second curved section 26. In the configuration example shown in FIG. 1, the curvature radius R6 of the distalmost section 27 is about 32 mm and its extension angle $\alpha 6$ is about 34°.

Figure 2:
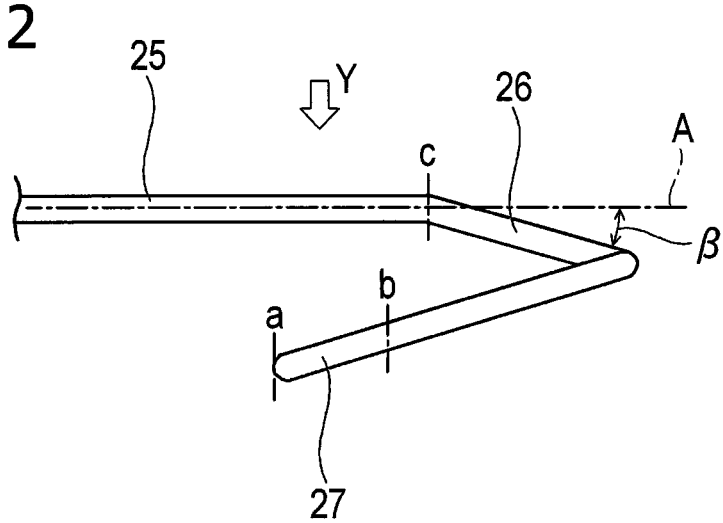
FIG. 2 is a view taken along an arrow X of FIG. 1.

As shown in FIG. 2, the second curved section 26 and the distalmost section 27 may be present on the plane A on which the proximal straight section 23, the first curved section 24 and the intermediate straight section 25 are present, or may be inclined so as to separate from the plane A. In the case where the second curved section 26 and the distalmost section 27 are inclined so as to separate from the plane A, and when the main body distal portion 22 is viewed from such a viewpoint that the main body distal portion 22 is located on the upper side of the main body proximal portion 21 and that the main body distal portion 22 is located on the right side of the main body proximal portion 21 (viewed along a direction of an arrow Y in FIG. 2), the second curved section 26 and the distalmost section 27 extend so as to deviate from the plane A obliquely toward the depth side (away from the viewer) from the plane A. An inclination angle $\beta$ of the second curved section 26 and the distalmost section 27 relative to the plane A is preferably set to be about 0 to 30°, for example. In the configuration example shown in FIG. 2, the inclination angle $\beta$ is about 10°. This inclination angle $\beta$ plays a role of facilitating the insertion of the distalmost section 27 into the left coronary ostium 102. Specifically, when the plane A on which the human aorta 103 is present (a plane on which the human ascending aorta 104 and brachiocephalic trunk 101 are present) is assumed, and when the aorta 103 and the left coronary ostium 102 are viewed from the front side of the aorta 103, the left coronary ostium 102 is located slightly to the viewer's side than the plane A on which the aorta 103 is present, whereas the distalmost section 27 and the second curved section 26 extend in a direction inclined relative to the plane A on which the first curved section 24 and the intermediate straight section 25 are present. Therefore, when the main body distal portion 22 is introduced into the aorta 103, even if the first curved section 24 and the intermediate straight section 25 are located on the plane on which the aorta 103 is located or are located on a plane parallel to the just-mentioned plane, the second curved section 26 and the distalmost section 27 are oriented toward the side of the left coronary ostium 102. Accordingly, the introduction of the distalmost section 27 into the left coronary ostium 102 can be carried out speedily, assuredly, and easily.

In addition, the second curved section 26 and the distalmost section 27, when projected on the plane A on which the proximal straight section 23, the first curved section 24, and the intermediate straight section 25 are present in a natural state, or the directions of curvature represented on the sheet of paper of FIG. 1, curve in the same direction as the first curved section 24.

Figure 3:
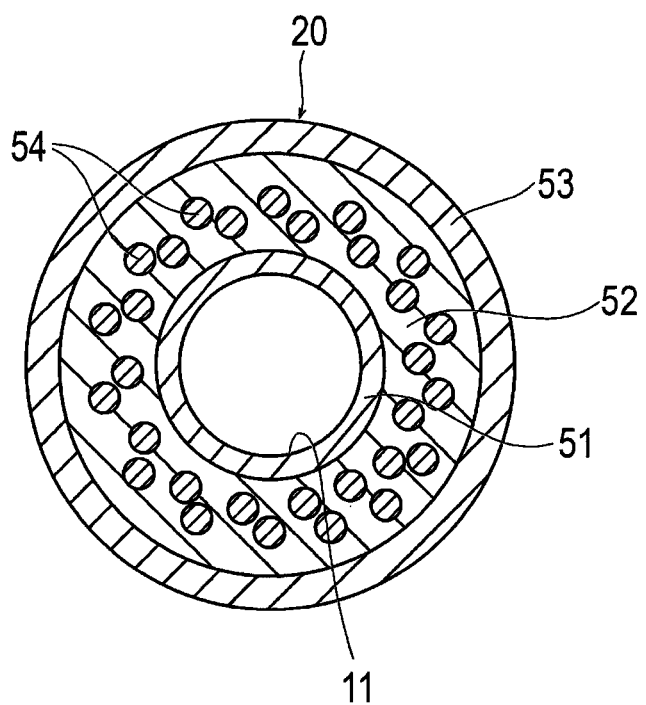
FIG. 3 is a sectional view taken along a line 3-3 of FIG. 1.

As shown in FIG. 3, the coronary artery catheter 10 has a structure in which a lumen 11 opening at the distal end is formed in a substantially central portion of the catheter body 20.

Besides, the catheter body 20 has a structure in which an inner layer 51, a middle layer 52, and an outer layer 53 are concentrically laminated in this order from the inside toward the outside. Such a configuration promises setting of desirable characteristic properties; for example, it ensures that the catheter body 20 is restrained from bending sharply.

Examples of materials which can be used to form the inner layer 51, the middle layer 52 and the outer layer 53 include polyamide resins (e.g., nylon 11, nylon 12, nylon 6), polyester polyamide resins (e.g., Grilax (trade name) produced by DIC Corporation), polyether polyamide resins (e.g., Pebax (trade name) produced by Atochem), polyurethane, ABS resin, polyester elastomer resins, polyurethane elastomer resins, and fluoro-resins (PFA, PTFE, ETFE, etc.). Particularly, when ABS resin or nylon is used as the material for forming the inner layer 51, the middle layer 52 and the outer layer 53, it is possible to impart appropriate strength to the main body distal portion 22. In addition, when a fluoro-resin, preferably PTFE, is used to form the inner layer 51, maneuverability of a guide wire 40 (see FIG. 5) or a therapeutic catheter inserted in the lumen 11 is enhanced. Incidentally, since the insertion of the catheter 10 is conducted while checking its position under radioscopy, the material for forming the catheter body 20 is preferably admixed with a radiopaque material such as barium sulfate, bismuth oxide, and tungsten.

Besides, the thicknesses of the inner layer 51, the middle layer 52 and the outer layer 53 are not particularly limited. In the example shown in the drawings, the inner layer 51 is thinner than the middle layer 52 and the outer layer 53. In addition, the inner layer 51, the middle layer 52 and the outer layer 53 are adhered to one another by an appropriate adhesive, or fused (welded) to one another by heat, or integrally molded by coating molding or the like. The middle layer and the outer layer may be provided as one layer formed of a same constituent material.

In the middle layer 52, a metal mesh 54 as a reinforcement material is embedded along the whole circumference. The metal mesh 54 may be present in such a manner as to make contact with an outer surface of the inner layer 51. With respect to a longitudinal direction of the catheter 10, the metal mesh 54 is embedded to range over substantially the whole length of the catheter body 20, except for a distal portion of a predetermined length from the distal end of the catheter body 20. The position of the distal end of the metal mesh 54 is preferably set in a range of 0.5 to 150 mm (preferably 1 to 100 mm) from the distal end of the catheter body 20 toward the proximal side.

With such a metal mesh 54 embedded, the catheter body 20 can be prevented from bending sharply, and torque transmission properties at the time of rotating the catheter body 20 can be enhanced. The cross-section of a wire constituting the metal mesh 54 is not specifically restricted, and may be circular, roughly rectangular, or roughly elliptic in shape.

The structure in which the metal mesh 54 is not embedded in the distal portion of the predetermined length from the distal end of the catheter body 20 ensures that damaging of a blood vessel wall by a distal portion of the catheter 10 can be restrained. The structure also ensures that flexibility can be imparted to the distal portion of the catheter 10, whereby the distal portion can be easily guided not into a left ventricle 110 but into the left coronary ostium 102. The length of the distal portion where the metal mesh 54 is not provided is appropriately determined according to the material of the catheter body 20, a difference between an inside diameter and an outside diameter of the catheter body 20 (the total thickness of the inner layer 51, the middle layer 52 and the outer layer 53), and the like.

Specific examples of the metal mesh 54 include those formed from thin wires (lines) of stainless steel, stainless spring steel, tungsten, Ni—Ti alloy, carbon fiber, or the like. The diameter of these wires or lines is, for example, about 0.01 to 0.2 mm.

Incidentally, the configuration of the catheter body 20 is not restricted to the above-mentioned. For example, a monolayer structure, a two-layer structure, or a four- or more-layered structure may also be adopted.

The coronary artery catheter 10 with its shape set as above-mentioned can have its distalmost section 27 engaged with the left coronary ostium 102 (or a right coronary ostium 107) from either an artery of an arm or a femoral artery.

Now, the operation and effect of the coronary artery catheter 10 according to the present embodiment will be described below. In the following, description will be made by taking as an example a case where the coronary artery catheter 10 is employed as a guiding catheter for use with a therapeutic catheter.

First, description will be made of a method in which the coronary artery catheter 10 according to the present embodiment is engaged with the left coronary ostium 102 by way of an aortic sinus 105 (see FIG. 5) by trans-radial intervention (TRI), which is a technique of introducing a catheter through the radial artery 100.

Figure 4:
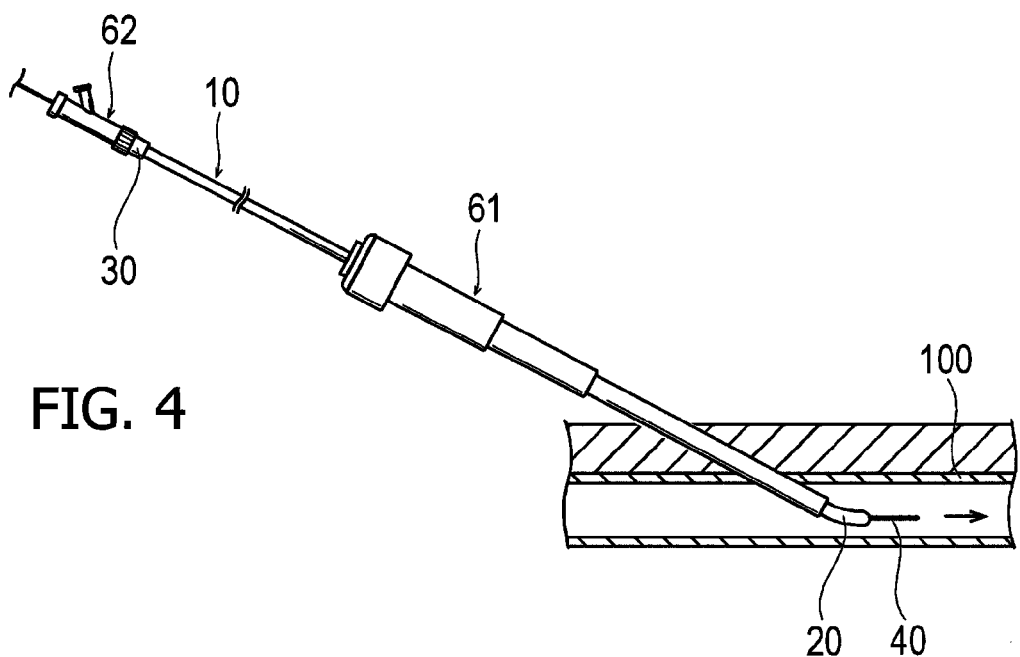
FIG. 4 is a schematic illustration of a method of introducing the coronary artery catheter according to the present embodiment into a blood vessel.

First, as shown in FIG. 4, a catheter introducer 61 is made to puncture the radial artery 100 by the Seldinger technique, and the catheter 10 with the guide wire 40 inserted in the lumen 11 is inserted into the catheter introducer 61. Then, in a condition in which the guide wire 40 is preceding the distal end of the catheter body 20, the distal end of the catheter body 20 is inserted into the radial artery 100 via a distal opening of the catheter introducer 61. Incidentally, the catheter 10 may be introduced not from the radial artery 100 but from a brachial artery.

Next, the catheter 10 and the guide wire 40 are gradually sent forward, to be gradually introduced through an aortic arch 108 of the aorta 103 into the ascending aorta 104, as shown in FIG. 5. In this case, in order that the distal end of the catheter body 20 can pass through bent portions of blood vessels, a combined operation in which send-in and send-out of the guide wire 40, forward and backward sending of the catheter 10, and rotation of the catheter 10 are repeated as required is carried out.

As shown in FIG. 5, the catheter 10 introduced through the brachiocephalic trunk 101 into the ascending aorta 104 is introduced into the vicinity of the left ventricle 110 of the heart. In this instance, the main body distal portion 22 of the catheter body 20 is in a substantially straight shape, since it is being stretched by the guide wire 40 inserted in the lumen 11.

Figure 6:
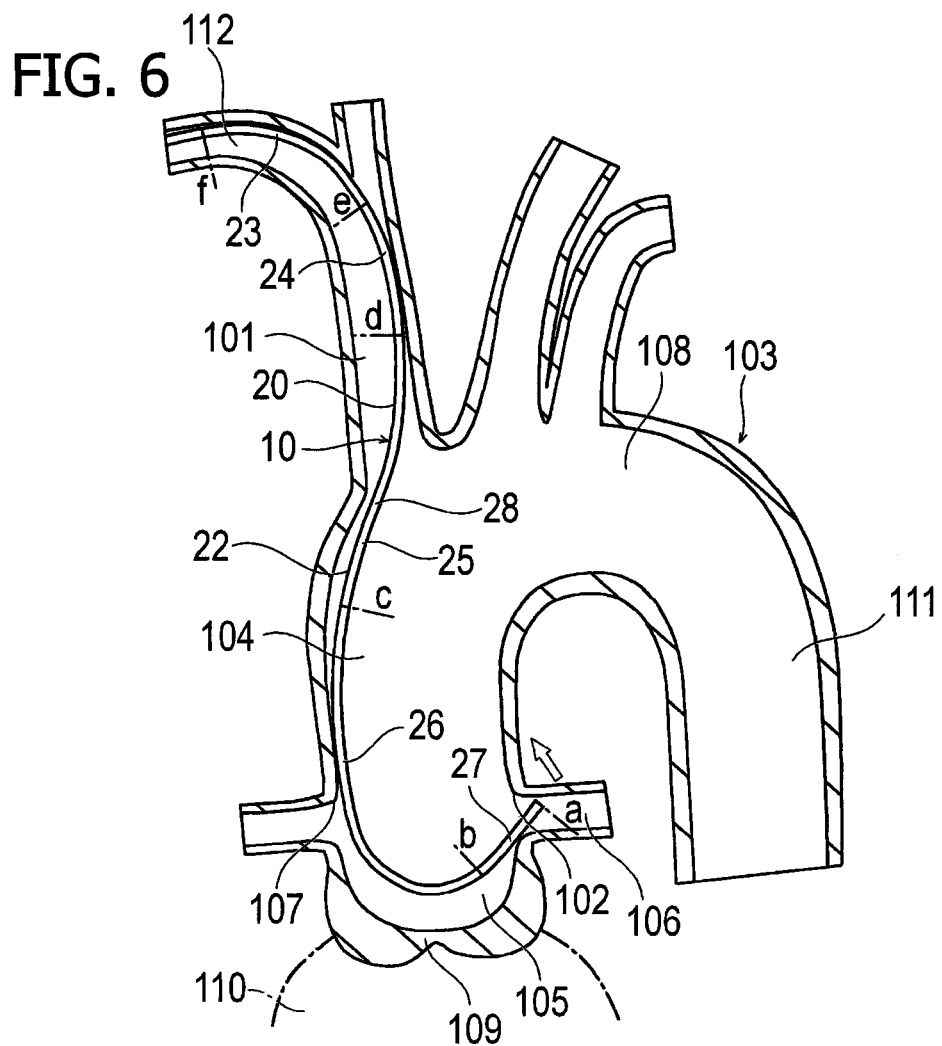
FIG. 6 is a schematic illustration of a state in which the coronary artery catheter according to the present embodiment is passed through the vicinity of an aortic sinus, and engaged with the left coronary ostium, that is introduced from the artery of the arm.

Thereafter, the guide wire 40 is pulled out of the catheter body 20, and thus the main body distal portion 22 returns into its original curved shape. By the resilience or repulsive force generated by the returning into the original shape, the distal end of the catheter 10 is oriented toward the left coronary ostium 102 (which is the opening of the left coronary artery 106), and is inserted into the left coronary ostium 102, as shown in FIG. 6. The distalmost section 27 is inserted into the left coronary ostium 102 by way of the aortic sinus 105 located more to an aortic valve 109 side than the left coronary ostium 102, of the ascending aorta 104, and is engaged with the left coronary ostium 102 in a state in which the axis of the distalmost section 27 is inclined relative to the axis of the left coronary artery 106. As a result, an outer surface of the distalmost section 27 makes point contact with an edge portion of the left coronary ostium 102, and the distalmost section 27 is engaged non-coaxially with the left coronary artery 106. Accordingly, the distalmost section 27 and part of the second curved section 26 are disposed drooping in the aortic sinus 105 while being curved in a same first direction and traversing a radial direction of the ascending aorta 104. In this instance, the catheter 10 may possibly make contact with the aortic valve 109.

Part of the second curved section 26 makes linear contact with, and is engaged with, an inner wall of the ascending aorta 104 which is located opposite to the left coronary ostium 102 (an inner wall on the right side of a patient), while being curved in the above-mentioned first direction. This part making the linear contact plays a role of backing up (i.e., supporting) the distalmost section 27 from the proximal side so that the distalmost section 27 engaged with the left coronary ostium 102 will not be disengaged.

The intermediate straight section 25 is disposed inside the ascending aorta 104 (the aorta 103) and inside the brachiocephalic trunk 101. The intermediate straight section 25 is in a state wherein its distal portion is curved in the first direction and having its proximal portion is a little curved in a second direction opposite to the first direction. In other words, the intermediate straight section 25 has an inflection point 28 located somewhere along its length at which the direction of curvature changes. The intermediate straight section 25 may make linear contact with inner walls of the ascending aorta 104 and the brachiocephalic trunk 101.

The first curved section 24 is disposed inside the brachiocephalic trunk 101 in a state of being curved in the second direction opposite to the direction of curvature in its original shape, like the proximal portion of the intermediate straight section 25. The first curved section 24 makes linear contact with, and is engaged with, the inner wall of the brachiocephalic trunk 101.

The proximal straight section 23 is disposed inside the brachiocephalic trunk 101 and/or inside the right subclavian artery 112 in a state of being curved in the second direction, like the first curved section 24, and makes linear contact with, and is engaged with, the inner wall of the brachiocephalic trunk 101 and/or the right subclavian artery 112.

Since the catheter 10 is disposed in the arteries in the above-mentioned manner, the catheter 10 is favorably supported in the arteries by the functions of the distalmost section 27 which is inserted in the left coronary artery 106 and engaged with the left coronary ostium 102, the second curved section 26 which is engaged with the inner wall of the ascending aorta 104 so as to play the role of backup (i.e., support), and the proximal straight section 23 which is engaged with the inner wall of the brachiocephalic trunk 101 and/or the right subclavian artery 112. Incidentally, the intermediate straight section 25 is so bent as to be a little curved in the second direction. In this case, the intermediate straight section 25 is bent in the second direction from a state of being straight in a natural state, and is not bent in the second direction from a state of being curved in the opposite direction (first direction) in a natural state. Therefore, the backup force (the force acting toward the depth of the left coronary artery 106) generated in this case is not as strong as the backup force generated in the case of a catheter in which a portion corresponding to the intermediate straight section 25 is curved in the first direction in a natural state. In addition, the intermediate straight section 25 has located therein the inflection point 28 at which the direction of curvature changes from the first direction into the second direction. Therefore, only a portion of the intermediate straight section 25 is bent in the second direction. This makes the backup force weaker, as compared with the case where the intermediate straight section 25 is wholly bent in the second direction.

However, the second curved section 26 is configured so as to have the curvature radius greater than the inside radius of the ascending aorta 104 and is set drooping inside the aortic sinus 105 (in the vicinity of the aortic valve 109) in a state of being deformed so as to temporarily increase (enlarge) the curvature radius of the second curved section 26. When the guide wire 40 is pulled out of the catheter body 20, a force for closing the thus broadened second curved section 26, or a force for clamping something between the distalmost section 27 and a proximal portion of the second curved section 26, is generated in the vicinity of the entrance to the left coronary artery 106 (see a void arrow in FIG. 6). Incidentally, if the curvature radius of the second curved section 26 is small, the second curved section 26 would be wholly contained in a space inside the aorta 103, so that such a clamping force is hardly generated. The generation of the clamping force, together with the fact that the backup force generated by the intermediate straight section 25 would not be excessively strong, ensures sufficiently strong engagement of the catheter 10 as a whole with the arteries. As a result, the main body distal portion 22 of the catheter body 20 is favorably fixed to the ascending aorta 104, and the distalmost section 27 is hardly disengaged from the left coronary ostium 102. Moreover, a situation in which the backup force generated by the intermediate straight section 25 is excessively strong is avoided, so that a phenomenon in which the distalmost section 27 is inserted excessively into the left coronary artery 106 (i.e., deep engagement) can be obviated. In addition, the distalmost section 27 is engaged with the left coronary artery 106 in an inclined manner. This promises more assured avoidance of the deep engagement phenomenon in which the distalmost section 27 is inserted excessively into the left coronary artery 106.

After the distalmost section 27 is inserted into the left coronary ostium 102 by the above-mentioned operations, a connector is connected to a Y connector 62 (see FIG. 4) mounted to a rear end of the hub 30, and a radiopaque material is injected. The radiopaque material thus injected passes through the lumen 11, and is jetted from the distal opening of the lumen 11 into the target site, namely, the inside of the left coronary artery 106. This enables checking of the insertion position of the catheter 10 in the left coronary ostium 102 and radioscopic imaging of the left coronary artery 106. Next, a therapeutic catheter (not shown) such as a PTCA balloon catheter can be inserted through a rear end portion of the Y connector 62 and through the lumen 11, and treatment can be performed. In this instance, the catheter 10 has its distalmost section 27 favorably engaged with the left coronary ostium 102, and has a favorable backup force. Consequently, counteractions arising from the insertion and operations of the therapeutic catheter can be relaxed, and the functions of the therapeutic catheter can be exhibited sufficiently.

Now, description will be made of a method in which the catheter 10 according to the present embodiment is engaged with the left coronary ostium 102 without passing through the aortic sinus 105, by the trans-radial intervention (TRI), which is a technique of introducing a catheter from the radial artery 100.

First, the catheter 10 with the guide wire 40 inserted in the lumen 11 is inserted into the ascending aorta 104 through the aortic arch 108 of the aorta 103, so as to reach the vicinity of the left ventricle 110 of the heart. This operation is conducted in the same manner as in the above-described method of engaging the catheter 10 with the left coronary ostium 102 by way of the aortic sinus 105 (see FIGS. 5 and 6). In this instance, the main body distal portion 22 of the catheter body 20 is in a substantially straight shape, since it is being stretched by the guide wire 40 inserted in the lumen 11.

Figure 7:
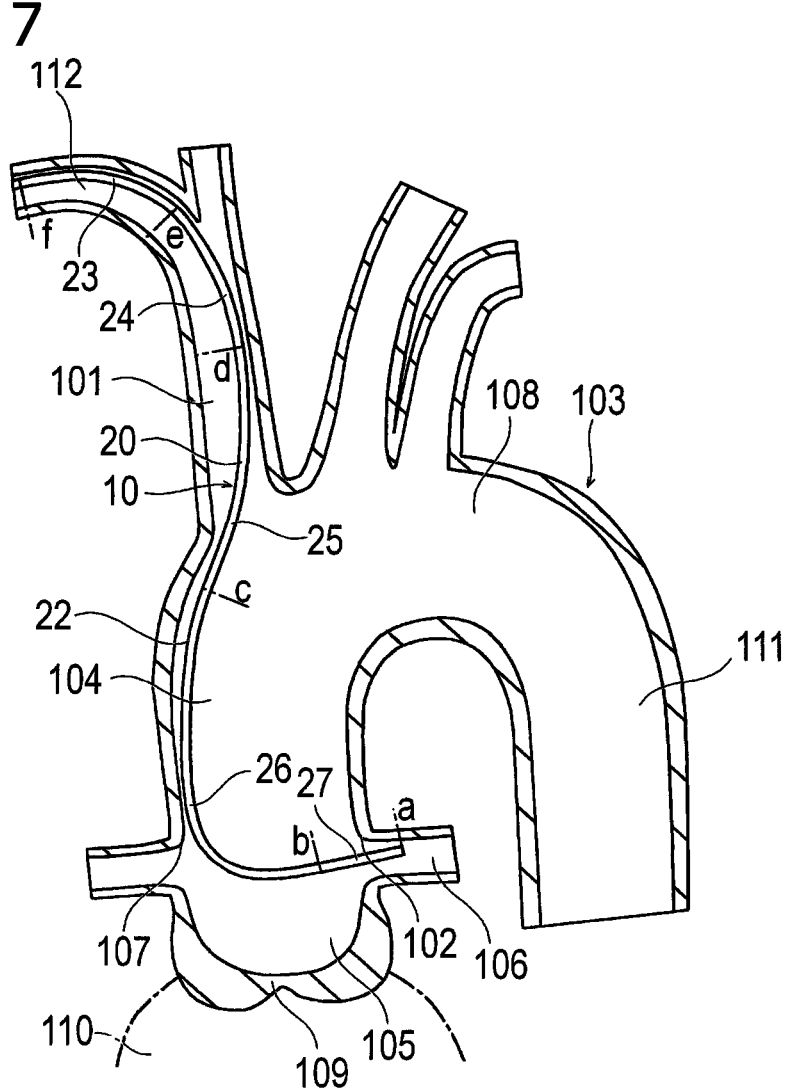
FIG. 7 is a schematic illustration of a state in which the coronary artery catheter according to the present embodiment is engaged with the left coronary ostium, that is introduced from the artery of the arm.

Thereafter, the guide wire 40 is pulled out of the catheter body 20, and thus the main body distal portion 22 returns into its original curved shape. By the resilience or repulsive force arising from the returning into the original shape, the distal end of the catheter 10 is oriented toward and inserted into the left coronary ostium 102, as shown in FIG. 7. The distalmost section 27 is inserted through the ascending aorta 104 into the left coronary ostium 102, and the axis of the distalmost section 27 is set substantially parallel to the axis of the left coronary artery 106. As a result, the distalmost section 27 makes linear contact with, and is engaged with, the inner wall of the left coronary artery 106. Therefore, the distalmost section 27 and part of the second curved section 26 traverse the radial direction of the ascending aorta 104, and part of the second curved section 26 makes linear contact with, and is engaged with, that inner wall of the ascending aorta 104 which is located opposite to the left coronary ostium 102 (the inner wall on the right side of the patient), while being curved in the first direction. This part of the second curved section 26 making the linear contact plays the role of backing up (i.e., supporting) the distalmost section 27 from the proximal side so that the distalmost section 27 engaged with the left coronary ostium 102 will not be disengaged.

The intermediate straight section 25 is disposed inside the ascending aorta 104 (the aorta 103) and inside the brachiocephalic trunk 101 in a state of being a little curved in the second direction opposite to the first direction. The intermediate straight section 25 may make linear contact with the inner walls of the ascending aorta 104 and/or the brachiocephalic trunk 101.

The first curved section 24 is disposed inside the brachiocephalic trunk 101, in a state of being curved in the second direction like the intermediate straight section 25. The first curved section 24 may make linear contact with, and be engaged with, the inner wall of the brachiocephalic trunk 101.

The proximal straight section 23 is disposed inside the brachiocephalic trunk 101 in a state of being curved in the second direction opposite to the direction of curvature in the shape in a natural state, like the intermediate straight section 25, and makes linear contact with, and is engaged with, the inner wall of the brachiocephalic trunk 101.

With the catheter 10 disposed inside the arteries as above-mentioned, the catheter 10 is favorably supported inside the arteries by the functions of the distalmost section 27 which is inserted in and engaged with the left coronary artery 106, the second curved section 26 which is engaged with the inner wall of the ascending aorta 104 and plays the role of backup, and the proximal straight section 23 which is engaged with the inner wall of the brachiocephalic trunk 101. Incidentally, the intermediate straight section 25 is so bent as to be a little curved in the second direction. In this case, the intermediate straight section 25 is bent in the second direction from the state of being straight in a natural state, and is not bent in the second direction from the state of being curved in the opposite direction (first direction) in a natural state. Therefore, the backup force generated in this case is not as strong as the backup force generated in the case of a catheter in which a portion corresponding to the intermediate straight section 25 is curved in the first direction in a natural state. In addition, although the distalmost section 27 is liable to be inserted into the depth of the left coronary artery 106 because the axis of the distalmost section 27 is substantially parallel to the axis of the left coronary artery 106, the phenomenon in which the distalmost section 27 is inserted excessively into the left coronary artery 106 (i.e., deep engagement) can be avoided because the backup force would not be excessively strong. Incidentally, the subsequent operations are the same as in the method of engaging the catheter 10 with the left coronary ostium 102 by way of the aortic sinus 105 by TRI. Therefore, descriptions of the subsequent operations are omitted here.

Now, description will be made below of a method in which the catheter 10 according to the present embodiment is engaged with the left coronary ostium 102 by transfemoral intervention (TFI), which is a technique of introducing a catheter through a femoral artery.

First, by the Seldinger technique, the catheter introducer 61 is made to puncture a femoral artery, and the catheter 10 with the guide wire 40 inserted in the lumen 11 is introduced into the catheter introducer 61. Then, in the state in which the guide wire 40 is preceding the distal end of the catheter body 20, the distal end of the catheter body 20 is introduced into the femoral artery via the distal opening of the catheter introducer 61.

Next, the catheter 10 and the guide wire 40 are gradually sent forward, to be gradually inserted into the ascending aorta 104 by first passing through a descending aorta 111 and the aortic arch 108 of the aorta 103. In this case, in order that the distal end of the catheter body 20 can pass through bent portions of blood vessels, an operation in which send-in and send-out of the guide wire 40, forward and backward sending of the catheter 10, and rotation of the catheter 10 are combined as required is carried out.

The catheter 10 introduced into the ascending aorta 104 is introduced into the vicinity of the left ventricle 110 of the heart. In this instance, the main body distal portion 22 of the catheter body 20 is in a substantially straight shape, since it is being stretched by the guide wire 40 inserted in the lumen 11.

Figure 8:
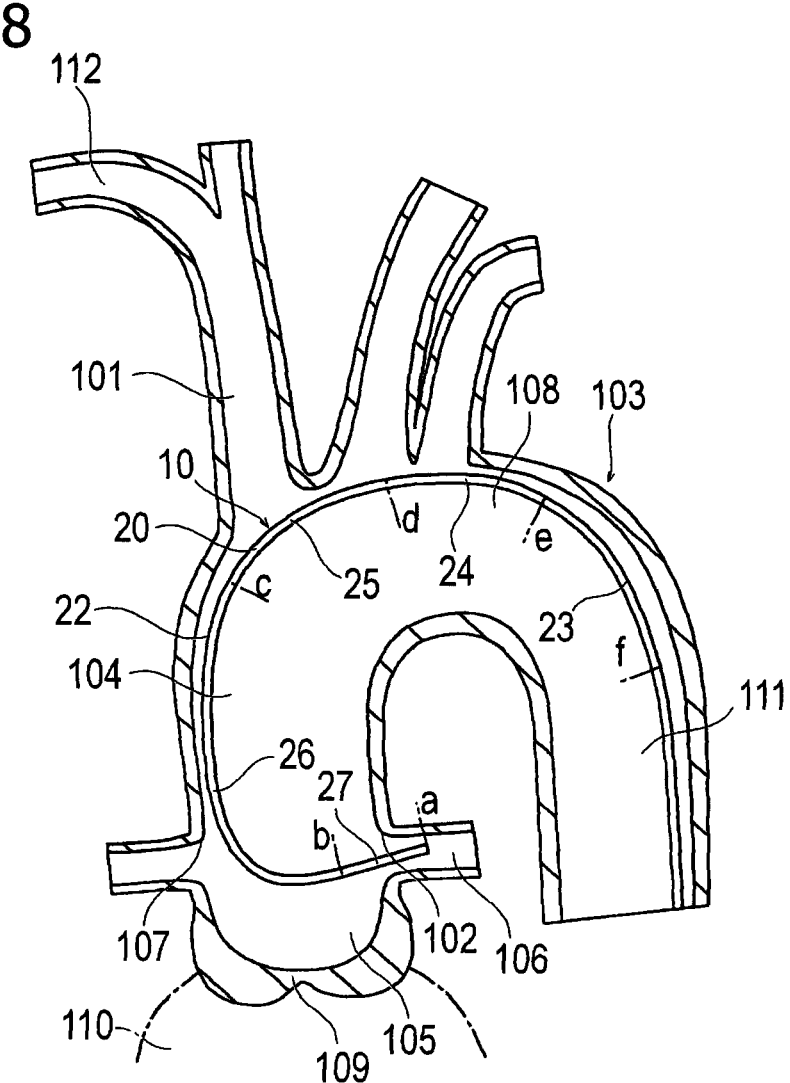
FIG. 8 is a schematic illustration of a state in which the coronary artery catheter according to the present embodiment is introduced from a femoral artery and is engaged with the left coronary ostium.

Thereafter, the guide wire 40 is pulled out of the catheter body 20, and thus the main body distal portion 22 returns into its original curved shape. By the resilience or repulsive force generated by the returning into the original shape, the distal end of the catheter 10 is oriented toward the left coronary ostium 102 and is inserted into the left coronary ostium 102, as shown in FIG. 8. The distalmost section 27 is inserted into the left coronary ostium 102 through the ascending aorta 104, and the axis of the distalmost section 27 is set substantially parallel to the axis of the left coronary artery 106. As a result, the distalmost section 27 makes linear contact with, and is engaged with, the inner wall of the left coronary artery 106. Then, the distalmost section 27 and part of the second curved section 26 traverse the radial direction of the ascending aorta 104. In addition, a proximal portion of the second curved section 26, the intermediate straight section 25, the first curved section 24, and a distal portion of the proximal straight section 23 are curved in the same first direction, and they make continuous and linear contact with and are engaged with the inner wall, opposite to the left coronary ostium 102, of the aorta 103 which includes the ascending aorta 104, the aortic arch 108 and the descending aorta 111. These sections making the linear contact play the role of backing up (i.e., supporting) the distalmost section 27 from the proximal side so that the distalmost section 27 engaged with the left coronary ostium 102 will not be disengaged.

Since the catheter 10 is disposed in the arteries in this manner, the catheter 10 is favorably supported in the arteries by the functions of the distalmost section 27 which is inserted in the left coronary artery 106 and engaged with the left coronary ostium 102, as well as the second curved section 26, the intermediate straight section 25, the first curved section 24, and the proximal straight section 23, which are engaged with the inner wall of the aorta 103 so as to play the role of backup. Incidentally, the second curved section 26, the intermediate straight section 25, the first curved section 24, and the proximal straight section 23 are curved in the first direction which is the same as the direction of curvature in their original shapes, so that they do not generate a strong backup force. In addition, although the distalmost section 27 is liable to be inserted into the depth of the left coronary artery 106 because the axis of the distalmost section 27 is substantially parallel to the axis of the left coronary artery 106, the phenomenon in which the distalmost section 27 is inserted excessively into the left coronary artery 106 (i.e., deep engagement) can be avoided because the backup force would not be excessively strong.

Incidentally, the subsequent operations are the same as in the technique based on the TRI in which the catheter 10 is introduced from an artery of an arm. Therefore, descriptions of the subsequent operations are omitted here.

As has been described above, the coronary artery catheter 10 according to the present embodiment has the catheter body 20 the lumen 11 therein. The catheter body 20, in a natural state, includes: the proximal straight section 23 being originally straight; the first curved section 24 extending distally from the proximal straight section 23 while being curved; the intermediate straight section 25 being originally straight and extending distally from the first curved section 24; the second curved section 26 extending distally from the intermediate straight section 25 while being curved; and the distalmost section 27 extending from the second curved section 26 to the distal end of the catheter body 20. The first curved section 24 and the second curved section 26, when projected onto the plane A on which the first curved section 24 and the intermediate straight section 25 are present, curve in the same direction. Therefore, when the coronary artery catheter 10 is inserted through an artery of an arm and the distalmost section 27 is engaged with the left coronary ostium 102, it is ensured that, while at least part of the second curved section 26 is kept in contact with the inner wall of the ascending aorta 104 opposite to the left coronary ostium 102 so as to function as a backup support, the first curved section 24 can be bent and the resilience or repulsive force generated by the bending can be exerted on the distalmost section 27 through the intermediate straight section 25 as a backup force. As a result, an appropriate backup force can be realized.

In addition, when the coronary artery catheter 10 is introduced by way of an artery of an arm and the distalmost section 27 is engaged with the left coronary ostium 102 (see FIGS. 6 and 7), the intermediate straight section 25 is disposed both inside the aorta 103 and inside the brachiocephalic trunk 101, whereas the first curved section 24 is disposed inside the brachiocephalic trunk 101. Therefore, while the first curved section 24 is bent inside the brachiocephalic trunk 101 in the direction opposite to the direction of curvature in a natural state so as to generate a backup force, an appropriate backup force can be transmitted distally by way of the intermediate straight section 25 which is disposed both inside the aorta 103 and inside the brachiocephalic trunk 101.

Further, when the coronary artery catheter 10 according to the present embodiment is introduced through an artery of an arm and the distalmost section 27 is engaged with the left coronary ostium 102 by way of the aortic sinus 105, as shown in FIG. 6, the catheter body 20 is favorably supported inside the arteries by the functions of the distalmost section 27 which is engaged with the left coronary ostium 102, the second curved section 26 which is engaged with the inner wall of the ascending aorta 104, and the proximal straight section 23 which is engaged with the inner wall of the brachiocephalic trunk 101 or the right subclavian artery 112. In addition, the distalmost section 27 extends toward the left coronary ostium 102 from that position in the ascending aorta 104 which is located more to the aortic valve 109 side than the left coronary ostium 102. This ensures that the axial of the distalmost section 27 is inclined relative to the axis of the left coronary ostium 102. As a result, a force for clamping something between the distalmost section 27 and the second curved section 26 (see the void arrow in FIG. 6) is generated in the vicinity of the left coronary ostium 102, so that the distalmost section 27 will hardly be disengaged from the left coronary ostium 102. Besides, the intermediate straight section 25 is provided with the inflection point 28 along its length, which restrains generation of an excessive backup force. Moreover, the axis of the distalmost section 27 is inclined relative to the axis of the left coronary ostium 102. These ensure that the catheter body 20 is restrained from being inserted excessively into the left coronary artery 106.

When the coronary artery catheter 10 according to the present embodiment is introduced through an artery of an arm and the distalmost section 27 is engaged with the left coronary ostium 102 without passing through the aortic sinus 105, as shown in FIG. 7, the catheter body 20 is favorably supported inside the arteries by the functions of the distalmost section 27 which is engaged with the left coronary ostium 102, the second curved section 26 which is engaged with the inner wall of the ascending aorta 104, and the proximal straight section 23 which is engaged with the inner wall of the brachiocephalic trunk 101 or the right subclavian artery 112. In addition, since the intermediate straight section 25 which is straight in shape in a natural state is bent, the generation of an excessive backup force is restrained, so that excessive insertion of the catheter body 20 into the left coronary artery 106 is restrained.

Besides, when the coronary artery catheter 10 according to the present embodiment is introduced through a femoral artery and the distalmost section 27 is engaged with the left coronary ostium 102, as shown in FIG. 8, the catheter body 20 is favorably supported inside the arteries by the functions of the distalmost section 27 which is engaged with the left coronary ostium 102, as well as the second curved section 26, the intermediate straight section 25, the first curved section 24, and the proximal straight section 23 which are engaged with the inner wall of the aorta 103. Incidentally, the second curved section 26, the intermediate straight section 25, the first curved section 24 and the proximal straight section 23 are curved in the same direction as their direction of curvature in a natural state, so that they are restrained from generating an excessive backup force. Consequently, excessive insertion of the catheter body 20 into the left coronary artery 106 is restrained.

The present invention is not to be restricted only to the above-described embodiment, and various modifications can be made by those skilled in the art within the scope of the technical thought of the invention. For instance, while the distalmost section 27 is engaged with the left coronary ostium 102 in the above description of the coronary artery catheter 10 according to the present embodiment, the distalmost section 27 can be engaged also with the right coronary ostium 107. In addition, the main body proximal portion 21 may not necessarily be straight in shape.

What is claimed is:

1. A method of engaging a coronary artery catheter, adapted for introducing a distal end of the coronary artery catheter into a coronary ostium through an artery of an arm, with the coronary ostium, wherein the coronary artery catheter has a catheter body with a lumen formed therein, the catheter body in a natural state including a proximal straight section being originally straight, a first curved section extending distally from the proximal straight section while being curved, an intermediate straight section being originally straight and extending distally from the first curved section, a second curved section extending distally from the intermediate straight section while being curved, wherein the second curved section has a curvature radius that decreases from the proximal end toward a distal end and part of the second curved section makes linear contact with, and is engaged with, an inner wall of an ascending aorta, which is located opposite to a left coronary ostium, and a distalmost section extending from the second curved section to a distal end of the catheter body, with directions of curvature of the first curved section and the second curved section projected onto a plane on which the first curved section and the intermediate straight section are present coinciding with each other, the method comprising:

engaging the distalmost section with the coronary ostium;

bringing the second curved section into linear contact with the inner wall of the ascending aorta opposite to the coronary ostium;

disposing the intermediate straight section both inside the ascending aorta and inside a brachiocephalic trunk; and disposing the first curved section inside the brachiocephalic trunk.

2. The method according to claim 1, wherein at least one of the second curved section and the distalmost section is inclined relative to the plane on which the first curved section and the intermediate straight section are present.

3. The method according to claim 1, wherein the distalmost section is curved.

4. The method according to claim 1, further comprising:

disposing a hub at the proximal end of the catheter body, the main body proximal portion extending distally from the hub.

* * * * *